United States Patent [19]

Bang et al.

[11] Patent Number: 6,066,465
[45] Date of Patent: May 23, 2000

[54] PROCESS FOR THE DIAGNOSTIC ASSESSMENT AND MONITORING, AS WELL AS MEDICAMENTS FOR THE THERAPY OF STATES OF SHOCK IN HUMANS

[75] Inventors: Holger Bang, Erlangen; Kay Brune, Marloffstein; Albrecht Wendel, Tuebingen; Gesa Tiegs, Constance, all of Germany

[73] Assignee: Paz Arzneimittel-Entwicklungsgesellschaft mbH, Frankfurt am Main, Germany

[21] Appl. No.: 08/817,096
[22] PCT Filed: Sep. 30, 1995
[86] PCT No.: PCT/EP95/03881
§ 371 Date: Jun. 3, 1997
§ 102(e) Date: Jun. 3, 1997
[87] PCT Pub. No.: WO96/12184
PCT Pub. Date: Apr. 25, 1996

[30] Foreign Application Priority Data

Oct. 12, 1994 [DE] Germany .............................. 44 36 352

[51] Int. Cl.$^7$ ...................... G01N 33/53; G01N 33/5661; A61K 38/51; A01N 37/18
[52] U.S. Cl. .......................... 435/7.92; 424/94.5; 435/7.4; 436/16; 436/501; 514/2
[58] Field of Search ............................ 424/94.5; 435/7.4, 435/7.92; 436/16, 501; 514/2

[56] References Cited

U.S. PATENT DOCUMENTS

| 4,722,999 | 2/1988 | Handschumacher et al. | 530/412 |
| 5,047,512 | 9/1991 | Handschumacher et al. | 530/402 |
| 5,447,852 | 9/1995 | Friedman et al. | 435/69.7 |
| 5,604,105 | 2/1997 | Jackowski | 435/7.4 |

OTHER PUBLICATIONS

Bochner et al., "Anaphylaxis" *The New England Journal of Medicine*, vol. 342(25):1785–1790, (1991).

Barron, Pathophysiology of Septic Shock And Implications for Therapy, *Clinical Pharmacy*, vol. 12:829–845, (1993).

Galat, "Peptidylproline cis–trans–isomerases: Immunophilins", *Eur. J. Biochem.*, vol. 216:689–707, (1993).

De Boer et al., "Interplay Of Complement And Cytokines In The Pathogenesis Of Septic Shock", *Immunopharmacology*, vol. 24:135–148, (1992).

Bang et al., "Interleukin–8 Is A Cyclosporin A Binding Protein", *Experientia*, vol. 49:533–538, (1993).

*Primary Examiner*—James C. Housel
*Assistant Examiner*—Rodney P. Swartz
*Attorney, Agent, or Firm*—Foley & Lardner

[57] ABSTRACT

A method is provided for detecting shock by measuring the concentration of cyclophilins in a patient's blood and comparing the measured concentration against a control. The severity of shock is then evaluated, an increase in cyclophilin concentrations over control levels being associated with severity. Measuring methods include enzymological techniques, such as rotomase activity assay; immunological procedures, such as radioimmunoassay and ELISA; peptide chemical processes, such as affinity chromatography; and radiochemical approaches, such as contacting the sample with radioactive cyclosporin.

10 Claims, 1 Drawing Sheet

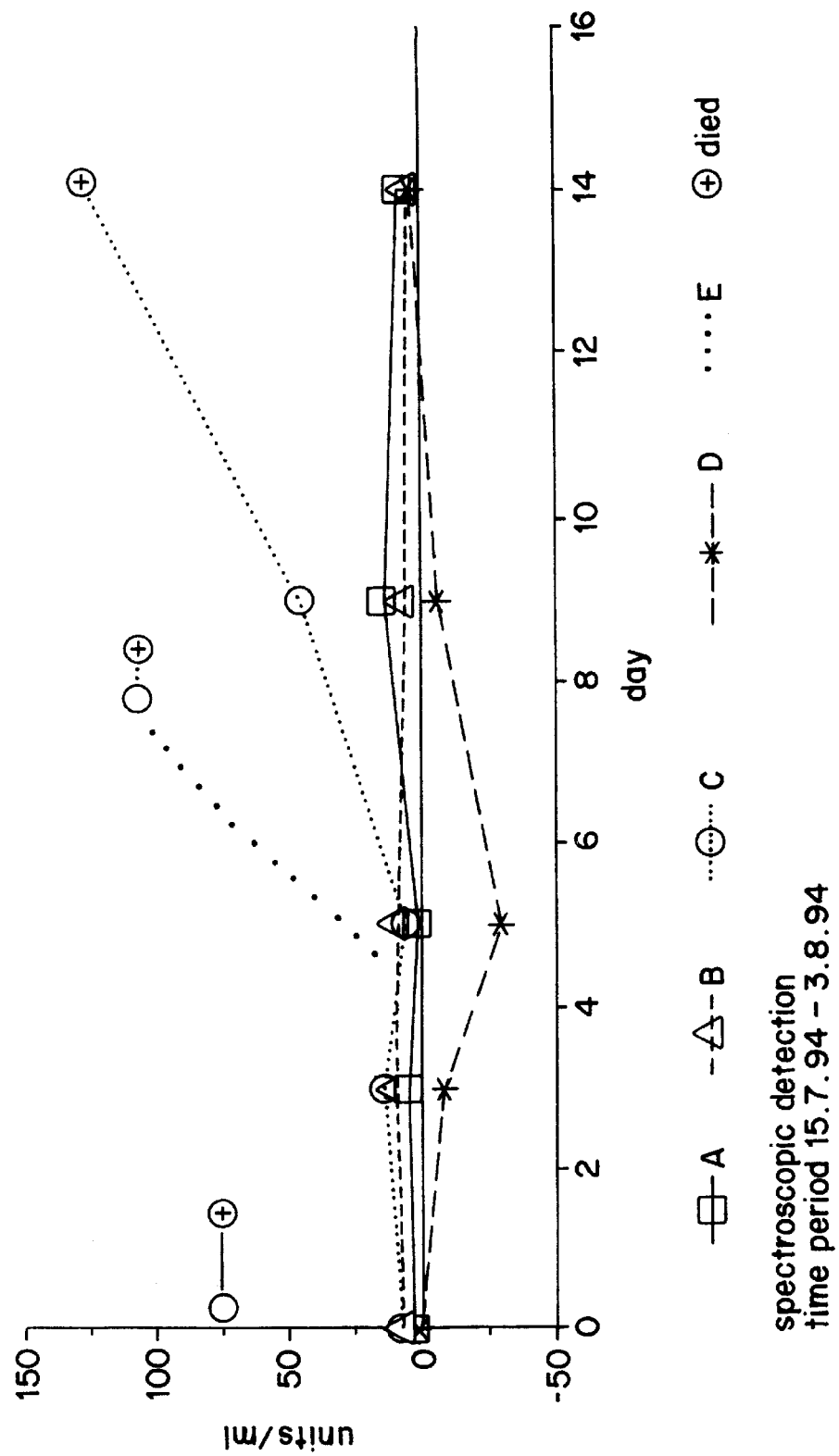

PROCESS FOR THE DIAGNOSTIC ASSESSMENT AND MONITORING, AS WELL AS MEDICAMENTS FOR THE THERAPY OF STATES OF SHOCK IN HUMANS

The subject of the present invention is a new process for the diagnostic assessment and monitoring, as well as a medicament for the therapy, of states of shock in humans.

BACKGROUND OF THE INVENTION

In the western industrial nations, every year thousands die directly from various forms of shock or the immediate results of the shock. As shock, one understands an acutely occurring, faulty regulation of the blood supply of vital organs due to blood pressure decrease. From this acutely occurring faulty regulation, there frequently develop diffuse or selective organ damages and protracted organ failure which, in about 10 to 30% of the cases, leads to death (cf., e.g., Pschyrembel, Klin. Wörterbuch, de Gruyter Berlin, 1992). Such shock reactions can occur on the basis of acute and chronic infections, in the case of pre-damaged patients (post-operative), treatment with cytostatics, etc. or also without recognizable cause, mostly as a result of otherwise harmless bacterial infections. One differentiates between anaphylactic, bacterial, septic, post-traumatic, cardiogenic, haemorrhagic, hypovolaemic, neurogenic and toxic forms of shock. A common factor appears to exist in the coexistence of an altered defense behavior of the body with regard to frequently harmless microbes on the basis of simultaneous and shortly previously occurring traumatic, surgical, immunological, medicamentous or toxic previous damaging of the organism (cf., e.g., Bochner, B. S. et al., N. Engl. J. Med., 1991, 3241 1785). Hitherto, a uniform and safe therapy process, especially of the post-traumatic, post-operative, toxic or septic shock has not existed (Barron, R. L., Clin. Pharm. 1993, 12, 829). Dependable criteria for the assessment of the prognosis and of the therapy success in the case of shock illnesses do not exist. Therefore, specific, recognized and rationally based therapy concepts have not been developed, presumably because of the absence of prognostic parameters.

Therefore, the task exists to find a new process for the diagnostic assessment and monitoring, as well as a medicament for the therapy, of states of shock in humans.

BRIEF DESCRIPTION OF THE DRAWINGS

FIG. 1 shows the concentration of cyclophilins in the blood of shock patients. Letters A–E designate individual patients.

DETAILED DESCRIPTION OF THE INVENTION

Surprisingly, in the case of the analysis of the blood of shock patients, it was found that some of them, shortly after beginning or in the further course of the shock illness, showed to a considerable extent cyclophilins in the serum of their blood. Patients who, at any point in time during the shock illness (between the first and fifteenth day), show cyclophilins in the serum to a clearly measurable extent died with great regularity in spite of intensive therapeutic efforts of the treating physician. Patients who survived showed, up to healing, at no point of time in measurable extent cyclophilins in the cell-free parts of their blood (serum, plasma, plasma fractions, etc.).

According to today's state of knowledge, all cells of the human and animal organism, as well as many bacteria, plant cells, etc., contain a special group of cytoplasmic proteins, the cyclophilins (Galat, A., Eur. J. Biochem. 1993, 216, 689). They serve to regulate protein folding, protein stability, protein liberation and also protein formation in connection with the regulation of the function of cells in the normal state or stress, such as, e.g., infections, transplant rejections etc. (Galat v. supra). Cyclophilins have been ascertained not only in the cytoplasm but also in the nucleus of eukaryotic cells (Galat v., supra). However, they do not normally occur in the extracellular medium and no important extracellular effects have been ascribed to them.

The here-reported observation contradicts the state of knowledge insofar as it is here reported for the first time that in connection with the shock illness, in the case of patients in which the shock occurrence finally led to death, already long before their death (days to weeks), considerable amounts of cyclophilins were detectable in the blood. Although the most differing mediators have been found in the case of, e.g., shock (de Boer, J. P., Immunopharmacology, 1992, 24, 135), cyclophilins have not been brought into conjunction with the shock occurrence.

The appearance of cyclophilins in the blood plasma or serum of shock patients is thus a pathognomonicly unfavorable sign. By monitoring this parameter in the serum, prognostic predictions can be made and the therapy monitored. A decrease of the cyclophilin concentration is to be regarded as a sign of possible therapy success; an increase, as a warning of an impending fatal result. Furthermore, in the case of experimentally induced shock states, the cyclophilin concentration can be used as a measurable variable for the verification of action of new forms of therapy.

Furthermore, the here-described surprising finding makes obvious that cyclophilins as mediators are themselves negatively active in the shock occurrences.

Cyclophilins have similarities with cytokines (Bang et al., Experientia, 1993, 49, 533), a group of substances which participate substantially in the defense preparedness of the human and animal organism. Therefore, their unexpected appearance outside cell boundaries could provoke a massive faulty regulation or reregulation of the defence preparedness of the human organism which are responsible for the immediate results of states of shock. For the therapy, it is, therefore, necessary to inactivate, antagonize or to remove the cyclophilins occurring in the case of shock patients. For this purpose, in principle, the following possibilities are available:

a) blockade or antagonization of the cyclophilins occurring in the blood plasma by blocking or antagonizing pharmaceuticals, b) blockade or antagonization of the cyclophilins occurring by biologically active materials, such as specific antibodies, anti-enzymes etc., c) removal and destruction of the cyclophilins occurring in the blood plasma or serum by physical and chemical methods, such as blood washing, etc.

The detection of the cyclophilins in the serum can take place with different methods, e.g., by enzymological methods, radiochemical methods, immunological methods and classical protein biochemical methods.

The mentioned diagnostic processes are in part known for the detection of the cyclophilins in cells; further processes are available for other indications and can be adapted to the here-described situations. For example, the cyclophilin concentration can be carried out by the measurement of the rotomase activity (peptide-proline-cis-trans-isomerism)

according to the following description (H. Bang, Dissertation, Halle, 1986, Wissenschaftsbereich Biochemie; Galat, supra and Fischer, G. et al., Biomed. Biochim Acta, 1984, 43, 1101):

Determination of Isomerism Activities in Body Fluids:

the analysis system depends upon the principle of the coupled spectroscopic enzyme test, i.e., the reaction of an auxiliary enzyme (chymotrypsin) is used for the detection of isomerases, by means of a protease (chymotrypsin), the conformation-specific reaction of a chromophoric peptide substrate is carried out and monitored spectroscopically, in a first, very rapid reaction, the protease selectively cleaves the trans-conformation, in a second, slower phase, the cis-conformation changes uncatalyzed into the trans-form and can thereafter be cleaved by the protease, isomerases, such as cyclophilins, selectively accelerate this cis-trans conversion, thus, in cell-free body fluids, isomerases can be analyzed via this spectroscopic detection, detection limit: nM of isomerism.

In a similar manner, with the help of the specific antibodies present against cyclophilins, according to the prior art, immunological, radio-chemical and other processes can also be developed.

In principle, as therapeutic process, a blockade of the cyclophilin with, e.g., cyclosporin A, an agent already used in transplantation medicine, rheumatism therapy, asthma therapy and the therapy, e.g., of psoriasis, is clinically usable. Its blocking action on cyclophilins can be verified in vitro.

In the case of the experimental animal (mouse), the giving of cyclosporin A (CsA) can prevent the lethal state of shock initiated by the injection of bacterial lipopolysaccharide (LPS) or TNFa (tumor necrosis factor a). The liver failure was quantified in this experiment by the detection of liver-typical enzymes, such as ALT (GPT), AST (GOT) and SDH (sorbitol dehydrogenase). The results are given in Table 1. The data were measured 8 hours after the treatment. The CsA was in each case injected 50 mg/kg i.v. 15 and 1 hour before the treatment.

TABLE 1

Protection by cyclosporin A against endotoxin- or TNFa-induced septic liver failure in galactosamine-sensitized mice.

|  | ALT [U/l] | AST [U/l] | SDH [U/l] |
| --- | --- | --- | --- |
| untreated control | 40 ± 4 | 70 ± 8 | 40 ± 5 |
| LPS (5 µg/kg) | 1500 ± 1025 | 1044 ± 620 | 544 ± 340 |
| CsA + LPS | 86 ± 61 | 160 ± 83 | 25 ± 20 |
| TNF (15 µg/kg) | 2650 ± 730 | 2190 ± 920 | 1345 ± 370 |
| CsA + TNFa | 260 ± 134 | 210 ± 68 | 71 ± 49 |

Results of Clinical Investigations

In FIG. 1 is shown concentration measurements of cyclophilins in the serum of 6 patients with shock illnesses. It is shown that, in the case of measurement of cyclophilins, in the case of use of the enzymatic detection method (peptide-proline-cis-trans-isomerism, PPlase test), they were detectable only in the case of patients who had increasing or increased amounts of cyclophilins in the plasma. Surprisingly, these intracellular proteins occurred to a clear extent already up to one week before the later death. They increase considerably before death. In contradistinction thereto, all three patients who survived the shock illness showed no measurable increase of the cyclophilin concentration in the serum.

Cyclophilin concentrations of above 50 U/ml appear, therefore, to point to a lethal ending of the shock situation, concentrations of above 20 U/ml to represent a clear warning signal.

Quantification and determination method:

The PPlase test is a method variable within limits with reference to the molecule structure of the substrate used and the proteolytic sensitivity of the PPlases, with which even PPlase activities can be determined quantitatively in only coarsely prepared biological materials. For human recombinate cyclophilin, the still detectable enzyme concentration which can be detected lies at about 0.5 ng cyclophilin per ml of serum. In rough approximation, about 1 nM cyclophilin corresponds to a concentration statement of 1 U/ml. In connection with what is said above, it follows that an increase of 5 U/ml thus represents a significant increase of the cyclophilin concentration and is clearly differentiable from a value of 0 U/ml.

Furthermore, in serum from sepsis patients, not only are clearly quantifiable amounts of cyclophilins ascertained (corresponds to positive values) but also modulators of the cyclophilins. In the case of a negative statement (–40 U/ml), it is a question of inhibitors. These values were determined by examination of the influence of sepsis blood on the cyclophilins given externally to the PPlase test.

Examples for the determination of the isomerism activity making available of cell-free serum;

use of a UV/VIS spectrophotometer with temperature controllable cuvette container (temperature controllable to 10° C.);

1 ml hepes buffer is pre-incubated with 1–20 µl of serum for 30 sec., thereafter 200 µl of the chymotrypsin solution are added thereto and immediately started with 5 µl of a substrate solution;

the reaction is continuously monitored for 3 min at a wavelength of 390 nm;

the speed constants of the observed reaction of 1st order is determined with the help of an evaluation program and corresponds to the U/ml used in the graph;

a measurement with evaluation requires about 10 min in the case of the present process.

What is claimed is:

1. A method of detecting a state of shock in a patient, comprising:

(a) providing a blood sample from a patient;

(b) measuring the concentration of cyclophilins in said blood sample;

(c) comparing the measured concentration of cyclophilins to a control; and (d) evaluating the degree of severity of shock, wherein an increase in cyclophilin concentration over control levels correlates with the severity of the shock.

2. A method according to claim 1, wherein said measuring is accomplished using an enzymological technique.

3. A method according to claim 2, wherein said enzymological technique is an assay of rotomase activity.

4. A method according to claim 1, wherein said measuring is accomplished using an immunological method.

5. A method according to claim 4, wherein said immunological method is a radioimmunoassay.

6. A method according to claim 4, wherein said immunological method is an enzyme-linked immunosorbant assay (ELISA).

7. A method according to claim 1, wherein said measuring is accomplished using a peptide chemical process.

8. A method according to claim 7, wherein said peptide chemical process comprises an affinity chromatography method.

9. A method according to claim 1, wherein said measuring is accomplished using a radiochemical method.

10. A method according to claim 9, wherein said radiochemical method comprises contacting the sample with radioactive cyclosporin.

* * * * *